United States Patent [19]

Ito et al.

[11] Patent Number: 4,705,812
[45] Date of Patent: Nov. 10, 1987

[54] PROCESS FOR PRODUCING POROUS FILMS INVOLVING A STRETCHING STEP AND THE RESULTANT PRODUCT

[75] Inventors: Keiko Ito, Nakatsugawa; Michiyasu Ito, Kuwana; Shoichi Tsuji, Nagoya; Hisatosi Suzuki, Okazaki, all of Japan

[73] Assignee: Mitsui Toatsu Chemicals, Inc., Japan

[21] Appl. No.: 681,914

[22] Filed: Dec. 14, 1984

[30] Foreign Application Priority Data

Mar. 5, 1984 [JP] Japan .................................. 59-40440
Mar. 22, 1984 [JP] Japan .................................. 59-53576
Mar. 22, 1984 [JP] Japan .................................. 59-53577

[51] Int. Cl.$^4$ ...................... B29C 67/20; B29C 55/10
[52] U.S. Cl. ......................................... 521/92; 264/41; 264/147; 264/154; 264/288.8; 264/290.2; 264/DIG. 13; 521/143
[58] Field of Search ......... 264/41, 147, 154, DIG. 13, 264/288.8, 290.2; 521/92, 143

[56] References Cited

U.S. PATENT DOCUMENTS 4,472,328  9/1984  Sugimoto et al. .................... 264/41

OTHER PUBLICATIONS

*The Encyclopedia of Patent Practice and Invention Management*, Robert Calvert, BDT, New York, Reinhold, ©1964, pp. 151-153.

*Primary Examiner*—Philip Anderson
*Attorney, Agent, or Firm*—McGlew and Tuttle

[57] ABSTRACT

A process for producing porous films which comprises melting a resin composition consisting essentially of (1) 100 parts by weight of a high-pressure-processed low-density polyethylene resin having a melt index of 0.5 to 7 and a density of 0.915 to 0.935, a linear low-density polyethylene resin having a melt index of 0.5 to 8.5 and a density of 0.915 to 0.935, or a mixture thereof and (2) 50 to 500 parts by weight of barium sulfate having an average particle diameter of 0.1 to 7 $\mu$m; forming the molten resin composition into a film; and then stretching the film at least uniaxially by a factor of 1.5 to 7. As the linear low-density polyethylene resin, a copolymer of ethylene and hexene and/or octene is particularly preferred.

10 Claims, No Drawings

PROCESS FOR PRODUCING POROUS FILMS INVOLVING A STRETCHING STEP AND THE RESULTANT PRODUCT

BACKGROUND OF THE INVENTION (a) Field of the Invention

This invention relates to an improved process for producing porous films. More particularly, it relates to a process for producing porous films which comprises blending a low-density polyethylene resin with barium sulfate as a filler, melting the resulting resin composition and forming it into a film, and then stretching the film at least uniaxially.

(b) Description of the Prior Art

Conventionally, there are a large number of well-known processes for producing porous films by forming a resin composition comprising a polyolefin resin and any of various noncompatible fillers into a film and then stretching this film. For example, Japanese Patent Laid-Open Nos. 47334/'82 and 203520/'82 disclose a process for producing porous films which comprises melting a resin composition obtained by blending a polyolefin resin with a filler and liquid rubber or a hydroxylated poly-saturated-hydrocarbon, forming the molten resin composition into a sheet or film, and then stretching this sheet or film. Moreover, Japanese Patent Laid-Open No. 15538/'83 discloses a process for producing porous films which comprises melting a resin composition obtained by blending a linear low-density polyethylene resin with a filler and a liquid or waxy hydrocarbon polymer, forming the molten resin composition into a sheet or film, and then stretching this sheet or film. However, the films produced by these processes are disadvantageous in that they exhibit surface tackiness due to the aforesaid component contained in addition to the polyolefin resin and the filler and in that they can only be practically used in relatively large thickness because of their low mechanical strength.

Furthermore, it is described in Japanese Patent Laid-Open No. 149303/'83 that such porous films can be used as a leakproof sheet in disposable diapers. Porous films for use as the leakproof sheet of a disposable diaper are produced by blending 100 parts by weight of a polyolefin resin with 28 to 200 parts by weight of a filler and 10 to 70 parts by weight of a liquid or waxy hydrocarbon polymer, forming the resulting resin composition into a film, and then stretching this film at least uniaxially by a factor of 1.2 or greater. However, this process for producing porous films has the disadvantages that some types of fillers give poor stretchability and hence fail to provide fully uniform pores and that the resulting film tends to produce a disagreeable noise. Moreover, the concurrent use of a hydrocarbon polymer makes this process unsatisfactory because the hydrocarbon polymer tends to bloom to the film surface and causes a sticky sensation.

Such porous films are also useful as a leakproof sheet in sanitary napkins. Conventionally, a sheet of paper which has been rendered liquid-impermeable by means of a synthetic resin such as polyethylene or the like has been used for this purpose. However, the resulting sanitary napkins have the disadvantage of causing a disagreeable sensation during prolonged use because of their lack of permeability to water vapor.

SUMMARY OF THE INVENTION

Accordingly, it is an object of the present invention to provide an improved process for producing porous films.

It is another object of the present invention to provide a process for producing porous films which have sufficiently high porosity and thereby exhibit high moisture permeability and gas permeability while retaining excellent water resistance.

It is still another object of the present invention to provide a process for producing porous films which are free from surface tackiness, have excellent softness and show little reduction in strength.

It is a further object of the present invention to provide an improved leakproof sheet for use in disposable diapers.

It is a further object of the present invention to provide an improved leakproof sheet for use in sanitary napkins.

Other objects of the present invention will be apparent from the following description.

According to the present invention, there is provided a process for producing porous films which comprises melting a resin composition consisting essentially of (1) 100 parts by weight of a low-density polyethylene resin comprising a high-pressure-processed low-density polyethylene resin having a melt index of 0.5 to 7 and a density of 0.915 to 0.935, a linear low-density polyethylene resin having a melt index of 0.5 to 8.5 and a density of 0.915 to 0.935, or a mixture thereof and (2) 50 to 500 part by weight of barium sulfate having an average particle diameter of 0.1 to 7 $\mu$m, forming the moleten resin composition into a film, and then stretching the film at least uniaxially by a factor of 1.5 to 7.

The expression "a resin composition consisting essentially of 100 parts by weight of a low-density polyethylene resin and 50 to 500 parts by weight of barium sulfate having an average particle diameter of 0.1 to 7 $\mu$m" as used herein means that the resin composition may further contain (1) at least one additive selected from common stabilizers, antioxidants, colorants, ultraviolet light absorbents and hydrocarbon-free lubricants and/or (2), in addition to the barium sulfate, other inorganic fillers (such as calcium carbonate and the like) or common inorganic and organic modifiers in an amount less than that of barium sulfate used (for example, not greater than 20% based on the amount of barium sulfate used), but the addition of liquid rubber, a hydroxylated poly-saturated-hydrocarbon or a hydrocarbon polymer as described in the aforementioned Japanese Patent Laid-Open Nos. 47334/'82, 203520/'82, 15538/'83 and 149303/'83 should be positively avoided in order to obtain a porous film free from surface tackiness.

According to the present invention, porous films which are free from surface tackiness and have excellent properties and which have been unobtainable in the prior art can be produced without using any of the above-described additives used in the prior art. This can be accomplished simply by specifying the type of the filler, its amount used and its average particle diameter, using a certain type of low-density polyethylene resin having a specific melt index and density, and stretching the film by a specific factor.

DETAILED DESCRIPTION OF THE INVENTION

The low-density polyethylene resins which can be used in the present invention include high-pressure-processed low-density polyethylene resins having a melt index of 0.5 to 7 and a density of 0.915 to 0.935 (although it is preferable to use a single resin, any blend of polyethylene resins having different densities may be used); linear low-density polyethylene resins having a melt index of 0.5 to 8.5 and a density of 0.915 to 0.935; and mixtures thereof. Preferably, the melt index is in the range of 1 to 5 for high-pressure-processed low-density polyethylene resins and 0.5 to 7 for linear low-density polyethylene resins. If the melt index is less than 0.5 or greater than 7 (8.5 for linear low-density polyethylene resins), the resin will have significantly decreased formability into a film and may fail to yield a film of small and uniform thickness.

On the other hand, if the density is lower than 0.915 or higher than 0.935, the resin will have decreased stretchability and increased rigidity and may fail to yield a soft film.

Particularly preferred low-density polyethylene resins are linear low-density polyethylene resins. Linear low-density polyethylene resins are copolymers of ethylene and one or more α-olefins, and differ from low-density polyethylene resins prepared by the conventional high-pressure process. Linear low-density polyethylene resins are prepared by the low-pressure process, and useful α-olefins include butene, hexene, octene, decene and the like. The difference between high-pressure-processed low-density polyethylene resins and low-pressure-processed low-density polyethylene resins lies in the fact that, when seen from the viewpoint of chemical structure, the former ones are highly branched polymers while the latter ones are straight-chain polymers. Among such linear low-density polyethylene resins, copolymers of ethylene and hexene and/or octene are particularly preferred.

In the practice of the present invention, barium sulfate having an average particle diameter of 0.1 to 7 μm and preferably 0.5 to 5 μm is used. If the average particle diameter is smaller than 0.1 μm, well-defined pores cannot be obtained. On the contrary, if it is larger than 7 μm, the resulting film will have poor stretchability and, therefore, well-defined pores can hardly be obtained just as in cases where the average particle diameter is too small.

The barium sulfate is used in an amount of 50 to 500 parts by weight, and preferably 100 to 400 parts by weight, per 100 parts by weight of the low-density polyethylene resin. If the amount of barium sulfate used is less than 50 parts by weight, sufficiently high porosity cannot be obtained, while if it is greater than 500 parts by weight, the resulting film cannot be fully stretched because of its increased rigidity and, therefore, will show a reduction in porosity.

It is preferable to subject the barium sulfate to surface treatment with a fatty acid or a metallic salt thereof, silicone, silane, a resin acid or the like, because this treatment is effective in improving its dispersibility in the resin and producing well-defined pores.

So far as the effects of the present invention are not impaired, other inorganic fillers such as calcium carbonate and the like or common inorganic and organic modifiers may be used in addition to the barium sulfate. However, these additives should be used in an amount of not greater than 20% based on the amount of barium sulfate used.

Now, the present process for producing porous films will be specifically described hereinbelow.

According to the need, at least one additive selected from stabilizers, antioxidants, colorants, ultraviolet light absorbents and lubricants is added to a low-density polyethylene resin as defined above and barium sulfate. These ingredients are mixed with a Henschel mixer, supermixer or tumbling mixer. Thereafter, using an ordinary single-screw or twin-screw extruder, the resulting mixture is blended and pelletized. Then, using an inflation extruder or T-die extruder, these pellets (alone or in admixture with low-density polyethylene resin pellets) are melted at a temperature higher than the melting point of the low-density polyethylene resin (preferably, by 20° C. or more) and lower than the decomposition temperature thereof, and formed into a film. In some cases, the aforesaid mixture may be directly formed into a film with an extruder, instead of being pelletized. Subsequently, the film is at least uniaxially stretched by a factor of 1.5 to 7 according to a conventional technique such as roll stretching, tentering or the like. This stretching may be performed in steps and/or in two or more directions. In the case of biaxial stretching, however, it is preferable to stretch the film simultaneously in the two directions. In order to enhance the morphological stability of pores, the stretched film may be annealed by heating.

The porosity is determined by the amount of barium sulfate used, the stretching factor and the like. If the stretching factor is less than 1.5, sufficiently high porosity cannot be obtained, while if it is greater than 7, a porous film cannot be steadily produced because of its frequent breakage during the stretching process.

Porous films produced by the process of the present invention are characterized by high porosity, excellent softness and little reduction in strength.

Moreover, since the good affinity between the low-density polyethylene resin and barium sulfate provides good stretchability, not only good workability but also an even distribution of pores can be achieved and, therefore, a porous film can be produced steadily. Especially when a linear low-density polyethylene resin is used as the base resin, the resulting film will show very little reduction in strength. Thus, it is possible to produce porous films which are thinner (for example, approximately 10 μm in thickness) than those produced by the prior-art processes.

Furthermore, since the resin composition does not contain any of the liquid rubber, hydroxylated polysaturated-hydrocarbons and hydrocarbon polymers used in the prior-art processes, the resulting porous film is free from surface tackiness.

Thus, the porous films of the present invention have sufficiently high porosity and hence exhibit good moisture permeability and gas permiability while retaining excellent water resistance, so that they can be used in clothing and sanitary applications. In addition, they can also be used as a filtering medium owing to their even distribution of pores.

The present invention is further illustrated by the following examples. However, these examples are given for purposes of illustration only and are not to be construed to limit the scope of the invention.

In the examples, melt index (MI) was determined according to ASTM D-1238 and density was determined according to ASTM D-1505.

Also in the examples, film properties were evaluated according to the following procedures:

(1) Strength and elongation

Using a Tensilon tensile testing machine, a piece of film measuring 25 mm (wide)×100 mm (long) is tested at a straining rate of 200 mm/min. Its strength and elongation at breakage are determined with respect to the machine direction (MD) and the transverse direction (TD).

(2) Moisture permeability

Moisture permeability is tested according to ASTM E96(D).

(3) Softness

Softness is evaluated by the feel and rated according to the following criteria:

A = Very soft and smooth.
B = Rather soft and smooth.
C = Hard and rough.

EXAMPLES 1–16 AND COMPARATIVE EXAMPLES 1–9

Each of the fillers given in Table 1 was added to the corresponding base resin in the amount given in Table 1, and mixed therewith by means of a Henschel mixer. Thereafter, using a twin-screw mixer, the resulting mixture was intimately blended and formed into pellets. Then, using a T-die extruder, these pellets were melted at a temperature 80° C. higher than the melting point of the base resin and formed into a film. This film was uniaxially or biaxially (Example 3) stretched by the factor given in Table 1 to obtain a porous film having the thickness given in Table 1. However, the film was not stretched in Comparative Example 1 and could not be stretched into a porous film in Comparative Examples 2 and 9. In Comparative Examples 5 and 8, the film could only be stretched by a factor of up to 2. In Comparative Examples 3 and 7, no sampling was possible because of frequent breakage during the stretching process.

The strength, elongation, moisture permeability and softness of the porous films thus obtained were evaluated according to the above-described procedures and the results are shown in Table 1.

TABLE 1

| | Base resin | | | | | Filler | | | Stretching factor | Film thickness (μm) | Strength(kg/25 mm) | | Elongation(%) | | Moisture permeability (g/m²/24 hr) | Softness |
|---|---|---|---|---|---|---|---|---|---|---|---|---|---|---|---|---|
| | Type[1] | Trade name (manufacturer) | Melt index (g/10 min) | Density (g/cm³) | | Type | Average particle diameter (μm) | Amount[2] (phr) | | | MD | TD | MD | TD | | |
| Example 1 | LDPE | Rexlon F-41 (Nippon Petrochemicals Co., Ltd.) | 5.0 | 0.923 | | BaSO₄ | 0.8 | 150 | 4 | 40 | 6.0 | 1.5 | 80 | 350 | 3,500 | A |
| Example 2 | " | Rexlon F-41 (Nippon Petrochemicals Co., Ltd.) | " | " | | " | " | " | 5 | " | 6.5 | 1.3 | 60 | 300 | 4,200 | A |
| Example 3 | " | Rexlon F-41 (Nippon Petrochemicals Co., Ltd.) | " | " | | " | " | " | 2 × 2 | " | 4.9 | 4.5 | 200 | 200 | 3,900 | A |
| Example 4 | " | MIRASON 45 (Mitsui Polychemicals Co., Ltd.) | 1.5 | 0.920 | | " | 1.2 | 130 | 5 | 50 | 5.5 | 1.5 | 120 | 450 | 3,000 | A |
| Example 5 | " | MIRASON 45 (Mitsui Polychemicals Co., Ltd.) | " | " | | " | 5.0 | 120 | " | " | 5.0 | 1.3 | 100 | 390 | " | A |
| Example 6 | " | UBE POLYETHYLENE F0191 (Ube Kosan K.K.) | 0.9 | 0.912 | | " | 1.2 | " | 3[3] | " | 3.9 | 1.0 | 55 | " | 1,100 | B |
| Example 7 | " | Neo-zex 4330 (Mitsui Petrochemical Industries, Inc.)/UBE POLYETHYLENE VF430 (Ube Kosan K.K.) = 2/1 | 3.0 | 0.940 | | " | " | 100 | 4 | " | 4.5 | " | 50 | 200 | 2,000 | C |
| Example 8 | L-LDPE | NUCG-5511 (Nippon Unicar Co., Ltd.) | 1.0 | 0.920 | | " | " | " | " | 30 | 3.5 | 1.2 | 100 | 420 | 3,900 | C |
| Example 9 | " | NUCG-5511 (Nippon Unicar Co., Ltd.) | " | " | | " | " | 150 | 5 | 15 | 2.5 | 0.8 | 80 | 400 | 5,000 | A |
| Example 10 | " | Ultzex 2020L (Mitsui Petrochemical Industries, Inc.) | 2.1 | " | | " | 4.2 | 50 | 6.5 | 40 | 7.8 | 1.4 | 65 | 170 | 2,800 | A |
| Example 11 | " | Ultzex 2020L (Mitsui Petrochemical Industries, Inc.) | " | " | | " | 0.8 | 150 | 5 | " | 6.5 | 1.8 | 130 | 510 | 7,500 | A |
| Example 12 | " | Ultzex 2020L (Mitsui Petrochemical Industries, Inc.) | " | " | | " | 0.5 | 100 | 7 | 10 | 2.3 | 0.7 | 40 | 120 | 8,500 | A |
| Example 13 | " | Ultzex 2020L (Mitsui Petrochemical Industries, Inc.) | " | " | | " | " | 300 | 3 | 40 | 5.3 | 1.5 | 78 | 360 | 5,500 | A |
| Example 14 | " | Ultzex 3010F (Mitsui Petrochemical Industries, Inc.) | 1.3 | 0.930 | | " | 5.0 | 150 | 5 | 50 | 5.1 | 1.4 | 110 | 400 | 6,700 | A |
| Example 15 | " | Ultzex 2020L (Mitsui Petrochemical Industries, Inc.) | 2.1 | 0.920 | | " | 0.5 | 500 | 2 | 40 | 5.0 | 1.0 | 35 | 20 | 5,000 | A |
| Example 16 | " | Ultzex 2010J (Mitsui Petrochemical Industries, Inc.) | 8.0 | " | | " | 0.8 | 200 | 3 | " | 5.5 | 1.4 | 105 | 420 | 4,700 | A |

TABLE 1-continued

| | Base resin | | | | Filler | | | Stretching factor | Film thickness (μm) | Strength(kg/25 mm) | | Elongation(%) | | Moisture permeability (g/m²/24 hr) | Softness |
|---|---|---|---|---|---|---|---|---|---|---|---|---|---|---|---|
| | Type[1] | Trade name (manufacturer) | Melt index (g/10 min) | Density (g/cm³) | Type | Average particle diameter (μm) | Amount[2] (phr) | | | MD | TD | MD | TD | | |
| Comparative Example 1 | " | Ultzex 2020L (Mitsui Petrochemical Industries, Inc.) | 2.1 | " | " | 0.8 | 150 | Unstretched | 50 | 2.5 | 2.3 | 570 | 480 | 15 | A |
| Comparative Example 2 | " | Ultzex 2020L (Mitsui Petrochemical Industries, Inc.) | " | " | " | " | 600 | Unstretchable | — | — | — | — | — | — | — |
| Comparative Example 3 | " | Ultzex 2020L (Mitsui Petrochemical Industries, Inc.) | " | " | " | " | 150 | 8[4] | — | — | — | — | — | — | — |
| Comparative Example 4 | " | Ultzex 2020L (Mitsui Petrochemical Industries, Inc.) | " | " | CaCO₃ | 1.0 | " | 4 | 70 | 4.3 | 0.8 | 20 | 100 | 3,000 | C |
| Comparative Example 5 | " | Ultzex 2020L (Mitsui Petrochemical Industries, Inc.) | " | " | Glass beads | 1.2 | 120 | 2[5] | 50 | 1.5 | 0.7 | 140 | 290 | 30 | C |
| Comparative Example 6 | " | NUCG-5511 (Nippon Unicar Co., Ltd.) | 1.0 | " | BaSO₄ | " | 30 | 5 | 40 | 4.5 | 1.0 | 105 | 430 | 15 | C |
| Comparative Example 7 | " | NUCG-5511 (Nippon Unicar Co., Ltd.) | " | " | " | " | 100 | 8[6] | — | — | — | — | — | — | — |
| Comparative Example 8 | " | NUCG-5511 (Nippon Unicar Co., Ltd.) | " | " | Glass beads | " | " | 2[7] | 60 | 1.0 | 0.5 | 40 | 100 | 40 | C |
| Comparative Example 9 | LDPE | PETROSEN 207 (Toyo Soda Manufacturing Co., Ltd.) | 8 | 0.924 | BaSO₄ | " | 130 | Unstretchable | — | — | — | — | — | — | — |

Notes:
[1]LDPE = low-density polyethylene.
L-LDPE = linear low-density polyethylene.
[2]Parts by weight of the filler per 100 parts by weight of the base resin.
[3], [5] & [7]The maximum value at which stretching can be performed steadily.
[4] & [6]No sampling was possible because of frequent breakage during the stretching process.

Porous films produced by the process of the present invention have high porosity and excellent softness and, moreover, show little reduction in strength, so that they are very suitable for use as a leakproof sheet in disposable diapers. Although such a leakproof sheet is generally used as the outermost layer of a disposable diaper, a material (such as a common punched film or sterically embossed sheet) not impairing its moisture permeability may be superposed on the outer side of the leakproof sheet to impart a cloth-like appearance thereto.

In such disposable diapers, there may be used any of common liquid absorbers including fluff composed of pulp fibers, such fluff wrapped in absorbent paper or the like, polymeric absorbers having high water absorbency, and the like.

As the liquid-permeable sheet which will be in direct contact with the skin, there may preferably be used a non-woven fabric composed of polyester fibers, nylon fibers, polyolefin fibers or the like.

In addition, there may be used pressure-sensitive tapes for fastening the diaper, and elastic members (such as rubber members) provided along the side edges to prevent leakage.

Disposable diapers are made by placing a liquid absorber on the aforesaid leakproof sheet, and stacking a liquid-permeable sheet thereon.

In disposable diapers using the porous film of the present invention as the leakproof sheet, the outermost leakproof sheet has a large number of pores. Since these pores allow water vapor to pass therethrough while retaining water droplets, the skin of the infant is not dampened but kept in a dry state, resulting in little tendency to develop diaper rash. Moreover, they also have the advantages of being hardly torn because of their high strength and being soft enough to produce no disagreeable noise.

The following examples illustrate the use of the porous film of the present invention as a leakproof sheet in disposable diapers.

EXAMPLES 17–19 AND COMPARATIVE EXAMPLES 10–14

Barium sulfate having an average particle diameter of 1.5 μm or each of the other fillers given in Table 2 was added to 100 parts by weight of low-density polyethylene (LDPE) having a melt index (MI) of 3 (Examples 17 and 18) or linear low-density polyethylene (L-LDPE) having a melt index (MI) of 5 (Example 19 and Comparative Examples 10–14) in the amount given in Table 2, and mixed therewith by means of a Henschel mixer. Thereafter, using a twin-screw mixer, the resulting mixture was intimately blended and formed into pellets. Then, using a T-die extruder, these pellets were melted at 130° C. and formed into a film. The film was uniaxially stretched between a preheating roll heated to 50° C. and a stretching roll by the factor given in Table 2 to obtain a porous film having a thickness of 50 μm. Properties of the porous films thus obtained were evaluated and the results are shown in Table 2. Disposable diapers were made by placing a filling of fluffy pulp and a nonwoven polyester fabric on each of the porous films obtained in Examples 17–19 and Comparative Examples 10, 13 and 14, and then providing it with pressure-sensitive tapes and rubber members.

The disposable diapers of Examples 17–19 were superior in strength, moisture permeability and softness to those of Comparative Examples 10, 13 and 14, so that they produced only a slight rustling noise during used and felt comfortable to the touch. When these disposable diapers were tested by using them practically in infants, those of Examples 17–19 caused no rash on the skin of the wearer. In contrast, the disposable diapers of Comparative Example 10, 13 and 14 caused an extensive rash or a slight rash (Comparative Example 13).

EXAMPLE 20

Using a biaxial stretching machine heated to 70° C., the unstretched film formed in Example 17 was simultaneously stretched in both the machine and the transverse direction (by factors of 2×2) to obtain a porous film having a thickness of 50 μm. Properties of this porous film were evaluated and the results are shown in Table 2. Disposable diapers using this porous film as the leakproof sheet exhibited as good performance as those of Example 17.

EXAMPLE 21

The same resin composition as used in Example 17 was formed into a film. Using a roll heated to 50° C., this film was uniaxially stretched by a factor of 4 to obtain a porous film having a thickness of 15 μm. Properties of this porous film were evaluated and the results are shown in Table 2.

On the outer side of this porous film was superposed a LDPE film of 70 μm thickness having apertures of 1 mm diameter (2/cm$^2$) all over its surface. Disposable diapers using this composite material as the leakproof sheet also exhibited as good performance as those of Examples 17–19.

TABLE 2

| | Base resin | | Filler | | | | | |
|---|---|---|---|---|---|---|---|---|
| | Type | Amount (parts by weight) | Type | Amount (parts by weight) | Stretching factor | Strength [MD/TD] (kg/25 mm) | Moisture permeability (g/m$^2$/24 hr) | Softness |
| Example 17 | LDPE | 100 | BaSO$_4$ | 150 | 4 | 6.0/1.5 | 3,500 | A |
| Example 18 | " | " | " | " | 5 | 6.5/1.3 | 4,200 | A |
| Example 19 | L-LDPE | " | " | 200 | 3 | 5.5/1.3 | 4,600 | A |
| Example 20 | LDPE | " | " | 150 | 2 × 2 | 4.9/4.5 | 3,900 | A |
| Example 21 | L-LDPE | " | " | 200 | 4 | 6.7/0.9 | 4,700 | A |
| Comparative Example 10 | " | " | " | 150 | Unstretched | 2.3/2.2 | 15 | A |
| Comparative Example 11 | " | " | " | 600 | Unstretchable | — | — | — |
| Comparative Example 12 | " | " | " | 150 | 8(*) | — | — | — |
| Comparative Example 13 | " | " | CaCO$_3$ | " | 4 | 4.3/0.8 | 3,000 | C |
| Comparative | " | " | Glass | 120 | 2(**) | 1.5/0.7 | 30 | C |

TABLE 2-continued

|  | Base resin | | Filler | | | | | |
| --- | --- | --- | --- | --- | --- | --- | --- | --- |
|  | Type | Amount (parts by weight) | Type | Amount (parts by weight) | Stretching factor | Strength [MD/TD] (kg/25 mm) | Moisture permeability (g/m$^2$/24 hr) | Softness |
| Example 14 |  |  | beads |  |  |  |  |  |

*An attempt was made to stretch the film by a factor of 8, but no sampling was possible because of frequent breakage during the stretching process.
*The film could not be stretched by a factor of more than 2.

COMPARATIVE EXAMPLE 15

120 parts by weight of calcium carbonate having an average particle diameter of 1.2 μm and 20 parts by weight of a hydroxylated poly-saturated-hydrocarbon (Liquid Polybutadiene GI-2000; Nippon Soda Co., Ltd.) were added to 100 parts by weight of linear low-density polyethylene (L-LDPE) having a melt index (MI) of 5, and mixed therewith by means of a Henschel mixer. Thereafter, using a twin-screw mixer, the resulting mixture was intimately blended and formed into pellets. Then, using a 40 mm0 inflation extruder, these pellets were formed into a film. This film was roll stretched at 80° C. by a factor of 3.0 to obtain a porous film having a thickness of 50 μm. This porous film varied in moisture permeability according to the location and exhibited a slight degree of surface tackiness. Disposable diapers using this porous film as the leakproof sheet caused a slight rash on the skin of infants.

COMPARATIVE EXAMPLE 16

The procedure of Comparative Example 15 was repeated except that liquid polybutadiene (Nisso PBG; Nippon Soda Co., Ltd.) or rubbery EPR (Toughmer P0480; Mitsui Petrochemical Industries, Inc.) was used as the hydroxylated poly-saturated-hydrocarbon. Thus, there were obtained films having a thickness of 50μm. These porous films exhibited surface tackiness and varied in moisture permeability according to the location. Disposable diapers using each of these porous films as the leakproof sheet caused a slight rash on the skin of infants.

Porous films obtained by the process of the present invention have high porosity and excellent softness and, moreover, show little reduction in strength in spite of their small thickness, so that they are very suitable for use as a leakproof sheet in sanitary napkins. Conventional sanitary napkins are so constructed that a liquid absorber such as fluffy pulp, cotton, absorbent resin or the like is partially covered with a film of paper having been rendered liquid-impermeable by treatment with a synthetic resin such as polyethylene or the like and the resulting structure is then wrapped in a non-woven fabric. In sanitary napkins using the porous film of the present invention as the leakproof sheet, this leakproof sheet has a large number of pores which allow water vapor to pass therethough. Accordingly, they can keep the skin of the user in a dry state and cause no disagreeable sensation even during prolonged use.

The following examples illustrate the use of the porous film of the present invention as a leakproof sheet in sanitary napkins.

EXAMPLES 22-24

Barium sulfate having an average particle diameter of 0.8 μm was added to 100 parts by weight of linear low-density polyethylene (L-LDPE) having a melt index (MI) of 2.1 in the amount given in Table 3, and mixed therewith by means of a Henschel mixer. Thereafter, using a twin-screw mixer, the resulting mixture was intimately blended and formed into pellets. Then, using a T-die extruder, these pellets were melted at 230° C. and formed into a film. This film was uniaxially stretched between a preheating roll heated to 80° C. and a stretching roll by the factor given in Table 3 to obtain a porous film having a thickness of 20 μm. Properties of this porous film were evaluated and the results are shown in Table 3. Sanitary napkins were made by covering a filling of fluffy pulp partially with each of the porous films obtained in Examples 22-24, wrapping the resulting structure in a non-woven fabric and then heat sealing its overlapping portions. When these sanitary napkins and commercially available ones having a liquid-impermeable film of polyethylene-coated paper were comparatively tested by using them practically for prolonged periods of time, the sanitary napkins in accordance with the present invention did not cause a disagreeable, stuffy sensation.

TABLE 3

|  | Base resin | | Filler | | | | | |
| --- | --- | --- | --- | --- | --- | --- | --- | --- |
|  | Type | Amount (parts by weight) | Type | Amount (parts by weight) | Stretching factor | Strength [MD/TD] (kg/25 mm) | Moisture permeability (g/m$^2$/24 hr) | Softness |
| Example 22 | L-LDPE | 100 | BaSO$_4$ | 100 | 6 | 3.2/1.0 | 5,200 | A |
| Example 23 | " | " | " | 150 | 5 | 3.0/0.9 | 4,800 | A |
| Example 24 | " | " | " | 400 | 3 | 2.5/0.8 | 4,200 | A |

What is claimed is:

1. In a process for producing porous films which comprises melting a resin composition consisting essentially of a polyethylene resin and a filler noncompatiable therewith, and with or without a hydrocarbon-free lubricant, forming the molten resin composition into a film and then stretching the film at least uniaxially, the improvement in which the polyethylene resin is either a high-pressure-processed low-density polyethylene resin having a melt index of 0.5 to 7 and a density of 0.915 to 0.935, a linear low-density polyethylene resin having a melt index of 0.5 to 8.5 and a density of 0.915 to 0.935, or a mixture thereof; the filler is barium sulfate having an average particle diameter of 0.1 to 7μm and the barium sulfate is used in an amount of 50 to 500 parts by weight per 100 parts by weight of the polyethylene resin; and the film is stretched by a factor of 1.5 to 7.

2. A process as claimed in claim 1 wherein the high-pressure-processed low-density polyethylene resin is a single resin.

3. A process as claimed in claim 1 wherein the high-pressure-processed low-density polyethylene resins having different densities.

4. A process as claimed in claim 1 wherein the melt index of the high-pressure-processed polyethylene resin is in the range of 1 to 5.

5. A process as claimed in claim 1 wherein the melt index of the linear low-density polyethylene resin is in the range of 0.5 to 7.

6. A process as claimed in claim 1 wherein the average particle diameter of the barium sulfate is in the range of 0.5 to 5 $\mu$m.

7. A process as claimed in claim 1 wherein the barium sulfate is used in an amount of 100 to 400 parts by weight per 100 parts by weight of the polyethylene resin.

8. A process as claimed in claim 1 wherein the barium sulfate has been subjected to surface treatment with a fatty acid or a metallic salt thereof, silicone, silane or a resin acid.

9. A porous film having water resistance, moisture permeability and gas permeability which has been produced by a process as claimed in any one of claims 1 and 2 to 8.

10. The porous film, according to claim 9, wherein said film is a fluid-impereable sheet for diapers or sanitary napkins.

* * * * *